United States Patent [19]

Czerlinski

[11] 4,454,234
[45] Jun. 12, 1984

[54] COATED MAGNETIZABLE MICROPARTICLES, REVERSIBLE SUSPENSIONS THEREOF, AND PROCESSES RELATING THERETO

[76] Inventor: George H. Czerlinski, 9111 Forest View Rd., Evanston, Ill. 60203

[21] Appl. No.: 335,736

[22] Filed: Dec. 30, 1981

[51] Int. Cl.$^3$ .............................................. B32B 5/16
[52] U.S. Cl. ................ 436/526; 252/62.54; 427/127; 427/216; 427/221
[58] Field of Search ...................... 252/62.54; 424/12; 436/526; 427/127, 216, 221

[56] References Cited

U.S. PATENT DOCUMENTS

| | | | |
|---|---|---|---|
| 3,970,518 | 7/1976 | Giaever | 195/1.5 |
| 4,018,886 | 4/1977 | Giaever | 424/12 |
| 4,070,246 | 1/1978 | Kennedy | 252/62.54 |
| 4,106,488 | 8/1978 | Gordon | 128/1 |
| 4,115,534 | 9/1978 | Ithakissios | 424/1 |
| 4,141,687 | 2/1979 | Forrest | 23/230 |
| 4,177,253 | 12/1979 | Davies | 424/1 |
| 4,247,406 | 1/1981 | Widder et al. | 252/62.54 |
| 4,267,234 | 5/1981 | Rembaum | 252/62.54 |
| 4,335,094 | 6/1982 | Moshach | 424/12 |

OTHER PUBLICATIONS

Nye et al., Solid-Phase, Magnetic Particle Radioimmunoassay, Clinica Chimica Acta. 69:387–396, (1976).
Nakamura et al., Magneto-Medicine: Biological Aspects of Ferromagnetic Fine Particles, J. App. Physics, 42:1320–1324, (1971).
Smith, M. L. in G. Herdan, Small Particle Statistics, Elsevier Publ. Co., Amsterdam, 1953, p. 471.
Narasimhan et al., Magnetic Properties of $RMn_2X_2$ Compounds, AIP Conf. Proc. 29:594, (1975).
Garen et al., Biochim. Biophys. Acta, 38:470, (1960).
Graham et al., Am. J. Pathol., 76:285, (1974).
Narasimham et al., J. Appl. Physics, 46:4957–4960, (1975).
Ito, Y., M. A. Weinstein, I. Aoki, R. Harada, E. Kimura and K. Nunogaki, Nature, 212:985, (1966).
Kronick et al. in Science, 200:1074–1076, (1978).
Avrameas et al., C. R. hebd. Seanc. Acad. Sci. Paris, Series D, 273:2705, (1971).

Primary Examiner—John F. Niebling
Attorney, Agent, or Firm—Tilton, Fallon, Lungmus

[57] ABSTRACT

Coated magnetizable particles of sub-micron size are used to form reversible suspensions in which the particles may be magnetically aggregated and thereafter resuspended as desired. Each microparticle comprises a core composed essentially of a magnetically-responsive material having a Curie temperature within the range of about 5° to 65° C. and a magnetic moment at saturation of at least 2.0 $\mu_B$ at 4.2° K., and a coating about the core formed of a solid cross-linked polymeric material having chemically reactive groups at the surface thereof.

18 Claims, No Drawings

COATED MAGNETIZABLE MICROPARTICLES, REVERSIBLE SUSPENSIONS THEREOF, AND PROCESSES RELATING THERETO

This invention was made with Government support under National Institutes of Health Research Grant No. 5 S07 RR-05370-16. The Government has certain rights in this invention.

BACKGROUND AND SUMMARY

Magnetic particles are known for use in laboratory and industrial procedures in which such particles are stationed or transported by applied magnetic fields. Where each particle is coupled to a selected biologically-active component, either as a matrix material or as a coating for the magnetizable particles, such particles may be effectively used in separatory procedures such as immunoassays and cell separations.

For example, solid-phase radioimmunoassay systems have been reported based on the use of antibodies covalently linked to polymer-coated iron oxide particles. An electromagnet is employed both to mix the particles during incubation (by switching the field on and off) and to separate the antibody-bound and free fractions. Nye, L., G. C. Forrest, H. Greenwood, J. S. Gardner, R. Jay, J. R. Roberts, and J. Landon, *Solid-Phase, Magnetic Particle Radioimmunoassay,* Clinica Chimica Acta, 69:387–396 (1976). Such techniques have not been free of problems and complications, however. Because of their relatively large size (well in excess of one micron) and high density (of the order of 5 gm/cc), the particles tend to settle rapidly under gravity unless vigorously stirred and also to "crush" large organic molecules. To reduce such problems, it has been proposed that such particles be formed as composites with the magnetizable component supporting, or supported by, a relatively low density non-magnetic component. See U.S. Pat. Nos. 4,177,253, 4,141,687, 4,115,534. By selecting a nonmagnetizable polymeric component having a density that will result in a composite particle whose density approximates that of the aqueous medium to be used, the stability of the suspension may be enhanced.

While the effective density of composite particles may thus be adjusted to suit the suspending medium, the relatively large size of such particles remains a disadvantage because of the smaller surface area per volume as compared with particles in the sub-micron size range. Also, in accordance with Stokes' Law on sedimentation, the sedimentation rate decreases with size; hence, particles of a size of 0.1 micron or less might (in the absence of aggregation) remain in suspension for periods of sufficient duration without continuous agitation, even though the density of the magnetizable material is substantially greater than that of the suspending medium. Unfortunately, small particles continually aggregate in a suspending medium in accordance with von Smoluchovski's Law of flocculation. That law neglects any gravitational or magnetic forces on the particles. Both would tend to increase the packing density of the particles with time, and the latter would also tend to orient and attract magnetized particles; both effects would accelerate aggregation. The practical result is that it becomes extremely difficult to resuspend sub-micron-sized particles of magnetically-susceptible material, especially particles of 0.1 micron or less in size, after such particles have been magnetically aggregated.

While it is known that certain larger particles in the size range of 1.0 to 4.0 microns may be separated and redistributed following magnetization if each particle is encapsulated in a shell of albumin having a thickness of about 0.1 micron, and that certain ferrofluids (particle sizes of about 0.01 micron) can be kept in suspension much longer than given by von Smoluchovski's Law if the material is chemically altered over the outer 10 to 15 Å, applicant is unaware of prior art teaching that magnetizable particles in the sub-micron size range, particularly those smaller than 0.1 micron but of domain size or larger, may be treated so that they may be readily resuspended following magnetic aggregation. Compare: Nakamura, T., K. Konno, and T. Morone, *Magneto-Medicine: Biological Aspects of Ferromagnetic Fine Particles,* J. App. Physics, 42:1320–1324 (1971); U.S. Pat. No. 4,247,406.

This invention is therefore concerned with coated magnetizable microparticles of an average size no greater than 1.0 micron in diameter, and preferably no greater than 0.1 micron in diameter, that may be magnetically aggregated in aqueous suspension and may then be resuspended without difficulty. Thus, in a biological separation procedure, the coated discrete microparticles may be dispersed in a fluid medium containing a component capable of reacting with the coating material, the particles then be exposed to a magnetic field under conditions causing magnetic aggregation of the particles, the aggregated particles may then be separated from the first liquid medium, introduced into a second liquid medium and resuspended in the absence of a magnetic field.

A major aspect of this invention lies in forming each sub-micron-sized particle so that it has a core composed of a magnetically-responsive material with a Curie temperature within the range of about 5° to 65° C., preferably 30° to 40° C., and a magnetic moment at saturation of at least $2.0\mu_B$ at 4.2° K. The aggregating and resuspending steps may therefore be undertaken in relation to the Curie temperature. Specifically, magnetic attraction between the particles, even if the cores thereof are formed of a material having ferromagnetic properties, will be dissipated by undertaking the resuspension step at or above the Curie temperature and in the absence of a magnetic field. Conversely, magnetic aggregation of the sub-micron-sized particles may be selectively achieved by exposing the particles to a magnetic field while such particles are held at a temperature approximating, or slightly below, the Curie temperature of the magnetizable core material.

A further aspect of the invention relates to the provision of a non-magnetic coating about each magnetizable core. The coating should preferably have a thickness of at least 100 Å or about 10% of the diameter of each microparticle, and in any event a minimum thickness of at least 10 Å, and most effectively comprises a water-insoluble cross-linked polymeric material having chemically reactive groups at the surface thereof. In the best mode known for practicing the invention, particle aggregation is inhibited by charged groups provided by the coating material at the periphery of the particles. The coating may be one or more layers with the exposed surface having whatever biological affinity or reactivity is required for a selected treatment or separation procedure, all as well known in connection with immunoassays, cell separation, and the like.

The core material should be ferromagnetic or ferrimagnetic at temperatures below Curie temperature, relatively brittle and not too hard (its hardness should not exceed 7, and preferably 6, on the Mohs scale), and generally compatible with both the coating and the fluid medium in which such particles are to be suspended. As stated, its Curie temperature must be within the range of 5° to 65° C., preferably 30° to 40° C., and the magnetic moment at saturation should be at least $2.0\mu_B$ at 4.2° K. A lanthanum-manganese-germanium alloy ($LaMn_2Ge_2$) has been found effective, but other alloys and oxides having ferromagnetic or ferrimagnetic properties, and Curie temperatures within the specified range, may be used. More specifically, ferrites, yttrium iron garnets, and alloys of $RMn_2X_2$, where R is a rare earth and X is germanium or silicon, may be used as long as the specified Curie temperatures and other requirements are met.

Other objects, advantages, and features of the invention will be apparent from the detailed specification.

DETAILED DESCRIPTION

The core material for forming the sub-micron-sized particles is a magnetically-responsive alloy or oxide having a Curie temperature within the general range of 5° to 65° C. and, especially for biomedical applications, within the preferred range of 30° to 40° C. Alloys of manganese having the general formula $RMn_2X$, where R is a rare earth, particularly lanthanum, cerium, praseodynium, or neodynium, and X is either germanium or silicon, are believed particularly suitable for the additional reason that they may be coated by a suspension polymerization process described in Example 1 herein. $LaMn_2Ge_2$ has a Curie temperature of about 33° C. and other alloys of this group have Curie temperatures as follows: $LaMn_2Si_2$ (30° C.), $CeMn_2Ge_2$ (43° C.), $PrMn_2Ge_2$ (61° C.), $NdMn_2Ge_2$ (61° C.). Magnetizable oxides having Curie temperatures within the specified ranges, such as certain yttrium iron garnets, may also be suitable. A scandium-substituted yttrium iron garnet of the formula $\{Y_3\}[ScFe](Fe_3)O_{12}$ has a Curie temperature at 21° C., and a zirconium-substituted yttrium iron garnet of the formula $\{Y_2Ca\}[ZrFe](Fe_3)O_{12}$ has a Curie temperature of 15° C. Other substituted yttrium iron garnets and their Curie temperatures are $\{Y_3\}[Mn_{.85}Fe_{1.15}](Fe_{2.15}Si_{.85})O_{12}$ (27° C.) and $\{Y_{2.80}Ca_{.20}\}[Mg_{.90}Fe_{1.10}](Si_{1.10}Fe_{1.90})O_{12}$ (21° C.). Another usable oxide, a ferrite of proprietary composition marketed as special ferrite by Ceramic Magnetics, Inc., Fairfield, N.J., has a Curie temperature of approximately 35° C. All of these magnetically-responsive materials have magnetic moments greater than $2.0\mu_B$ at saturation field strengths. Such materials also have specific gravities well above 3.0 and, hence, substantially greater than the aqueous media in which the final particles will be suspended. Because of the thinness of the coatings, the average specific gravity of each final particle, considering both its core material and coating, will still exceed 3.0.

To reduce the particles of core material to the size required for producing coated microspheres or microparticles having average diameters no greater than 1.0 micron, and preferably no greater than 0.1 micron (but of domain size or larger), the core material should be sufficiently brittle to facilitate grinding. For the same reason, the hardness of the alloy or oxide should not exceed about 7 Mohs, and preferably not more than about 6 Mohs, in hardness. Fine grinding in an agate ball mill is particularly effective in reducing the particles to the desired size, but other known techniques for producing such extremely small size particles, such as chemical precipitation, might possibly be used. The suspending medium in a ball milling operation may be aqueous or non-aqueous and its selection will depend in part on the wetting characteristics of the solid material. For example, butanol has been found to be an effective wetting agent for $LaMn_2Ge_2$; in addition, it has also been found useful in suspension polymerization procedures involving microparticles of that alloy.

Uniformity of particle size is also important, particularly where they are to be used later in quantitative analytical procedures. More specifically, where the coated microparticles are to be used in biomedical procedures such as immunoassays, the core surface area of the largest particle in a mass of such discrete particles should not exceed twice the core surface area of the smallest of such particles. If the particles are considered as generally spherical, then core radii (diameters) should not differ by more than $\sqrt{2}$ overall. By so limiting the size range of the particles or, more accurately, their magnetizable cores, the accuracy of quantitative measurements during subsequent use of the particles will tend to be enhanced because the size differential is not great enough to cause a single particle to be attracted magnetically with the same force or at the same rate as two smaller microparticles taken in combination.

The particles and their cores may be functionally regarded as microspheres although it is to be understood that such assessment is intended to facilitate physical, chemical, and mathematical analysis and that in fact such particles and cores only approximate sphericity. Electron micrographs of the core particles and final coated particles generally reveal two different axis dimensions (diameters D and d) in the same plane and, in accordance with accepted practice, the estimated volume of such a particle may be determined (using the formula $d^2D\pi/6$) and, on the basis of such volume, the surface area of a true sphere may then be calculated.

To achieve a quantity of magnetic microparticles (or microcores) below the specified average size limits and within the prescribed size differential limits, successive pulverization (grinding) and fractionating steps are required. To avoid the possibilities of magnetic enhancement of the attraction that occurs between small particles in suspension as represented in von Smoluchovski's Law of flocculation, the pulverizing and fractionating steps should be carried out above the Curie temperature of the core material. Size fractionation may be carried out by sedimentation in a gravitational field as disclosed by M. L. Smith in G. Herdan, Small Particle Statistics, Elsevier Publ. Co., Amsterdam 1953, p. 471. A particularly efficient method, involving a rotating gravity coil, is described by Ito, Y., M. A. Weinstein, I. Aoki, R. Harada, E. Kimura and K. Nunogaki, Nature, 212:985 (1966). Since such fractionation procedures are fully disclosed in the art and are well known, a more detailed discussion is believed unnecessary herein. If desired, since the microparticles to be size fractionated are magnetically responsive, a magnetic field (gradient) may be used as a supplement or substitute for the gravitational field.

Coating of the magnetic microparticles, which then become the magnetizable cores for the final coated particles, should take place immediately following the completion of fractionation since the coating of the particles with a non-magnetic polymer prevents the sub-micron sized core particles from approaching to distances where crystal bonds might be formed between them. Also, since the magnetic properties of the core materials augment the tendency of the core particles to aggregate, it is important that the coating process, like the pulverization and fractionation processes before it, be undertaken at a temperature above the Curie temperature of the core material.

Any suitable coating procedure may be used. One such method is described by Kronick et al in Science, 200:1074–1076 (1978), although the core material disclosed therein (magnetite) has a Curie temperature far higher than the Curie temperatures of the core materials disclosed herein and, unlike applicant's method, the coating procedure is carried out well below the Curie temperature of magnetite. In the Kronick procedure, the magnetite in finely-divided form is used in a ferrous ion-persulfate redox polymerization system with the polymer forming around the magnetite particles and encapsulating them in beads of hydrogel. The reaction is initiated by ferrous ion diffusing from the particles and forming free radicals from unsaturated monomers by reduction of the persulfate in the surrounding solution. A more detailed description of such an emulsion polymerization procedure for forming an acrylic polymer coating about each particle, the coating including a biologically active cholera enterotoxin, as such procedure would be carried out using applicant's core materials and operating conditions, is set forth herein in Example 2.

A particularly effective method for coating the magnetic core particles is the suspension polymerization process described in Example 1. Unlike the emulsion polymerization process mentioned above, which requires two immiscible liquid phases with polymerization occurring at the liquid-liquid interface, the suspension polymerization procedure utilizes only a single liquid phase and polymer development is more effectively confined to the particle surfaces. The formation of undesirable polymeric interconnections between adjacent particles is thereby reduced or avoided, and the polymeric coatings of the particles tend to have greater regularity and definition.

In a suspension polymerization process, the magnetic microparticles, pulverized and fractionated as previously described, are homogenously distributed in a liquid phase composed of suitably substituted monomers. Polymerization is initiated from the surface of the particles because such particles include an element capable of attaining three oxidation states and of thus mediating single-electron initiation of polymerization with the aid of persulfate. For example, in the case of the alloys described above, manganese is the element capable of multiple stages of oxidation. The monomers used in the process may be any of a wide variety of materials capable of undergoing polymerization at any temperature above the Curie temperature of the core material and under conditions in which such polymerization would be initiated by free radicals at the surfaces of such particles. Acrylamide, N,N'-methylenebisacrylamide, N,N-ethylenebisacrylamide, n-butylacrylate, and N-acryloylglycine methyl ester have been found effective, but other monomers having similar properties may be used. In the case of a coating process utilizing acrylamide, N,N'-methylenebisacrylamide, and n-butylacrylate in the molar proportions of 4:2:1, postassium persulfate or ammonium persulfate is included to initiate polymerization, and n-butanol or other persulfate-compatible solvent, may be used as a solvent for the reactants. The reaction mixture is maintained in an oxygen-free (nitrogen) environment at a temperature above the Curie temperature of the core material. For example, where the core material is a lanthanum-manganese-germanium alloy described above, reaction temperatures within the range of 35° to 40° C. have been found effective, such reaction temperatures being well above the Curie temperature of 33° C. of such material.

Regardless of the particular coating process used, such coating process, like the pulverizing and fractionating steps that precede it, should be performed above the Curie temperature of the core material to reduce magnetic enhancement of agglomeration of such particles. The coating procedure should preferably be continued until the coating thickness of each of the microparticles is at least 100 Å or about 1/10 of the total diameter of each particle, with a minimum thickness in any event of about 10 Å. A coating of at least minimum thickness is required in order to overcome the undesirable effects of magnetic enchancement of particle aggregation (in the absence of a magnetic field) and to promote resuspension of the particles following magnetic aggregation of the coated particles, but the optimum thickness in any given instance will depend in part on other factors influencing the tendency for such particles to aggregate or remain suspended, namely, the average size (radius) of the cores, the suspending medium selected and the lyophobicity of the coating material in relation to it, the temperature at which the particles are to be suspended or resuspended, particularly with respect to magnetic remanence, and the surface charge of the coating and its density. With respect to the latter, the effectiveness of the coating in avoiding unintended agglomeration and promoting resuspension is increased if the polymerized coating material is reacted to produce charged surface groups. For example, in the case of an acrylic polymeric coating, the coating material may be reacted with a base to produce carboxyl groups or with a primary amine to form acid amides. Charged residues of such modified coatings promote reversibility of suspension in aqueous media and further diminish the tendency of such particles to aggregate. Such residues may also be used to covalently link the particles to other molecules, including proteins and immunoglobulins. Reference may be had to the Kronick et al citation above, and to other prior art identified herein, for known procedures for bonding biologically-reactive materials to the surfaces of the coated sub-micron particles.

Following the coating step, the particles may again be fractionated above Curie temperature, following the procedure described above but in an aqueous medium compatible with the coating material or materials, to eliminate particles that may have become aggregated or bonded together during the coating operations because of interparticle cross-linking of the polymeric shells. Such re-fractionation is particularly important where the particles are to be used in quantitative procedures.

In the use of the particles for immunoassays, cell sorting, and other laboratory procedures, temperature would normally be maintained at about, or slightly above, the Curie temperature of the particular core material used, at least until magnetic aggregation of the particles is desired. Magnetophoretic separation may occur at or slightly above the Curie temperature by exposing the reaction mixture to a magnetic field sufficient to cause magnetic migration and agglomeration of such particles. If the temperature is at or above Curie temperature, such magnetic aggregation and migration will occur only as long as the magnetic field is applied;

withdrawal of the inducing magnetic field will cause the attraction between the particles to dissipate because there is no (magnetic)remanence at or above the Curie temperature of the core material. Magnetic separation of a material capable of reacting with or binding to the coating of the particles may therefore be achieved simply by aggregating the reacted particles in a magnetic field, physically separating such particles from the fluid medium and other (non-magnetic) particles by maintaining and utilizing the magnetic field, and then resuspending the magnetically-separated particles by agitating such particles in a second fluid medium in the absence of a magnetic field. If necessary, in order to increase or enhance magnetic attraction between the coated particles during the separation step, the temperature of the particles may be lowered below the Curie temperature of the core material but, in that event, the temperature should again be increased to a temperature at about, or slightly in excess of, Curie temperature when resuspension of the particles in the second fluid medium is desired. Therefore, except for the step of magnetically aggregating the coated particles, during which step temperatures may be (but are not necessarily) reduced below the Curie temperature of the core material, the manipulative steps are carried out at about, or slightly above, such Curie temperature.

Reference may be had to the following illustrative examples relating to preparation and use of the coated magnetic microparticles of this invention.

EXAMPLE 1

Suspension polymerization of a coating of magnetic particles of sub-micron size may be carried out as follows:

25.6 mg of n-butylacrylate, 58.6 mg acrylamide, 61.6 mg N,N'-methylenebisacrylamide, and 10 mg $K_2S_2O_8$ are added with pure n-butanol under vigorous stirring to a reaction vessel under oxygen-free conditions, the vessel chamber having previously been flushed with pure nitrogen for 15 minutes. Nitrogen is further flushed over the solution and a stock suspension of $LaMn_2Ge_2$ particles having an average diameter of 0.1 microns in n-butanol is added to the monomer bath; final volume, 50 ml. Temperature of the particles and bath should be maintained at 37° C. Prior to being added to the bath, the particle suspension should be subjected to at least 10 minutes sonication at a temperature in excess of 33° C. After approximately 180 minutes, the reaction is stopped by admitting air to the reaction chamber, and coated particles are collected by centrifugation and washed three times with pure methanol. The methanolic suspension is then used for further modification of the reactive groups of the ester coating. The ester groups may be converted to carboxyl groups with KOH or to acid amide groups with primary amines such as 1,7-diaminoheptane in high excess.

EXAMPLE 2

Emulsion redox polymerization may be conducted as follows, in accordance with the procedure described by Kronick et al, Science 200:1074–1076 (1978): 20 mg of allylamine and 20 mg of fluorescein isothiocyanate are shaken together in 10 ml of 0.01 M borate buffer, pH 9.5, for one hour (this pre-reaction is only necessary if the incorporation of the fluorescence probe fluorescein is desired). This mixture is then reacted at room temperature for two hours with 1.4 g of hydroxyethylmethacrylate, 0.2 g of N,N'-methylenebisacrylamide, 0.4 g of methacrylic acid, 0.05 g of sodium pyrophosphate, 0.03 g of ammonium persulfate, and 0.05 g of powdered magnetite (Wright Industries, Brooklyn, N.Y.; 50 nm average diameter; supplied as slurry) in 50 ml of water at pH 3.9. The reactants are stirred under nitrogen in a round 100 ml flask with a paddle stirrer. The product beads are precipitated magnetically in a divergent 5000 G magnet, resuspended in 10 mM phosphate buffer at pH 7.0, and dialyzed against the same buffer.

Diaminoheptane spacer groups may be attached by reacting 13.5 ml of magnetic beads (18 mg dry weight per ml) in 10 mM phosphate buffer, pH 7.0 with 1.5 ml of 1,7-diaminoheptane and 100 mg of 1-ethyl-3-(3-dimethylaminopropyl-)carbodiimide, shaken with glass beads for five hours at 4° C. After dialysis against 0.1 M NaCl followed by 10 mM phosphate buffer at pH 7.0, the product is coupled to glutaraldehyde by adjusting the mixture to 1.2% content in redistilled glutaraldehyde. The reaction mixture is shaken with glass beads of 5 mm diameter at room temperature for 75 minutes and then dialyzed against 10 mM phosphate buffer at pH 7.0. The aldehyde-containing product should be used immediately (see Examples 3 and 4).

EXAMPLE 3

Bovine serum albumin (BSA) may be coupled to the glutaraldehyde-activated microspheres by reacting 50 mg of the coated microspheres with 1 mg of BSA in 2 ml of 5 mM phosphate buffer at pH 7.0, shaking with glass beads for 24 hours at 4° C. The BSA-coated particles are washed by centrifugation and resuspension three times into phosphate buffered saline (PBS).

Sheep antisera to rabbit-anti-BSA antibodies are obtained as described by Avrameas (S. Avrameas, Immunochemistry 6:43 (1969)). They are coupled to *Escherichia coli* alkaline phosphatase (Worthington Biochem, Freehold, N.J.) by the glutaraldehyde method described by Avrameas et al (S. Avrameas and B. Guilbert, C. r. hebd. Seanc. Acad. Sci. Paris, Series D 273:2705 (1971)). Rabbit anti-BSA antibodies are obtained as also described by Avrameas et al. Para-nitrophenyl phosphate (Calbiochem, San Diego, Cal.) as 1 mM in 1 M Tris-HCl pH 8 is used to measure the alkaline phosphatase activity. The reaction is stopped by adding 100 μl of 3 M $K_2HPO_4$ and measured at 410 nm (A. Garen and C. Levinthal, Biochim. Biophys. Acta 38:470 (1960)).

To measure rabbit anti-BSA antibodies, a given quantity (50 to 100 μg of BSA per 10 ml tube) of BSA-coated magnetic particles are added to a series of tubes. To each tube of 1 ml of rabbit antiserum adequately diluted (derived from preliminary tests) in PBS containing 2% (v/v) of normal sheep serum and 0.05% Tween 20 (medium 1) is added. After two hours of rotating the (closed) tubes at room temperature, the magnetic particles are collected with a magnet, washed with 4 ml of PBS containing 0.05% Tween 20 (medium 2). They are collected and resuspended a total of three times. Then 1 ml of alkaline phosphatase-labeled sheep anti-rabbit immunoglobulin (2 to 5 μg of antibody/ml) diluted in medium 1 is poured into each tube. The tubes are allowed to rotate at room temperature for two hours and the excess conjugate is then removed by three washings with medium 2. Para-nitrophenyl phosphate is then added, and the tubes are again closed and horizontally rotated for a time depending upon the amount of enzyme employed. The catalytic activity is finally measured at 410 nm. Very small quantities can in fact be measured with this method.

EXAMPLE 4

The aldehyde-containing product of Example 2 may be reacted with protein as follows: choleragen (cholera enteroxtoxin, Schwarz/Mann, Orangeburg, N.Y.) is attached to the "activated" spacer-groups by reacting 50 mg of coated microspheres with 1 mg of toxin in 2 ml of 5 mM phosphate buffer at pH 7.0, shaking with glass beads at 4° C. for 24 hours. The toxin-coated beads are washed by centrifugation and resuspension three times into phosphate-buffered saline (PBS). The final suspension contains 1 mg (dry weight) of magnetic microspheres per ml of PBS.

The method of Kronick et al (P. L. Kronick, G. LeM. Campbell and K. Joseph, Science 200:1074–1076 (1978)) may be followed using the toxin-coated magnetizable microparticles to separate cells from a line of neuroblastoma, some of which bear the ganglioside $G_{M1}$, for which choleratoxin is specific. The C-1300 neuroblastoma was investigated in vitro (D. I. Graham, N. K. Gonatas and F. C. Charalampous, Am. J. Pathol. 76:285 (1974)). A clone of this tumor grown in vitro demonstrates individual heterogeneity in the cell-surface expression of $G_{M1}$, as indicated by the binding of either horseradish peroxidase-conjugated choleragen, or choleragen-conjugated fluorescent magnetic microparticles. From 2 to $5 \times 10^6$ cells are incubated with 0.1 to 1.0 mg (dry weight) of choleragen-conjugated magnetic microspheres at 4° C. for 30 minutes. To remove excess unbound microspheres, the cell suspension is layered on top of fetal calf serum and centrifuged at $800 \times g$ for 10 minutes. This procedure is repeated twice. The cells are resuspended in 2 ml of Dulbecco's modification of Eagles basal medium (Grand Island Biolog. Co.) for the separation procedures.

The separations are completed in 1 to 6 minutes with a divergent 5000 G magnet. Magnetophoretically unfractionated samples contained 12.5 and 15.0% choleragen-positive cells, whereas the retained and eluted fractions contained 99.0 and 99.5 vs. 1.0 and 1.5%, respectively. At least 200 cells were counted for each run. The appearance of the magnetic particles on the cells was also shown electromicrographically.

EXAMPLE 5

Magnetic microparticles of $LaMn_2Ge_2$ suitable for use in the procedures of the foregoing examples may be prepared as follows:

10 g of the alloy $LaMn_2Ge_2$ were prepared according to the method of Narasimhan et al (K. S. V. L. Narasimhan, V. U. S. Rao, R. L. Bergner, and W. E. Wallace, J. Appl. Physics 46:4957 (1975)). Annealing at 700° C. was carried out for two weeks. X-ray analysis confirmed the desired structure. Initially, the exact amount of alloy was weighed: 10.53 g. To obtain an approximate value for the density of the material, a 5 ml graduated cylinder was filled with 3.0 ml n-butanol. After the addition of the weighed material, a volume of 4.6 ml was determined. The specific weight at room temperature was then determined by the ratio of the weight of the material to the volume occupied: 10.53 g: 1.6 ml = 6.58 g/cm$^3$.

The parts of the material weighed are then prepulverized in an Agate mortar of 75 mm outer diameter. Small amounts are used and a paper screen is employed to catch any particles ejected from the mortar. The grinding is done thus without loss of particles. The pre-pulverized material is added to a cleaned Agate mortar with the ball of 70 mm diameter removed. 10 ml of L-α-phosphatidyl choline (type III E of Sigma, 100 mg) in cyclohexane are added onto the powder. The cyclohexane is evaporated (under flow of air) and the mortar brought into a room of 37° C. temperature. 3 ml of a mixture of 50% Witcamide in n-butanol (v/v) are added and the automatic mortar is started (amplitude 5, Pulverisette 0 of Tekmar). After two days, another 1.5 ml of the liquid mixture are added.

The mortar is stopped after 143 hours, 20 ml of liquid mixture are added, and grinding is continued for another 10 minutes (mainly to obtain a homogeneous suspension). The Agate ball of 70 mm diameter is then withdrawn and the contents of the mortar are transferred into a sedimentation bottle. More liquid mixture is used for the transfer of the suspension. The volume in the bottle is filled up to the 200 ml mark (118 mm liquid column). A stopper is added and the liquid is thoroughly shaken. The bottle is then rested for sedimentation at 37° C.

After seven minutes the stopper is carefully replaced by a syphoning assembly (avoid any stirring; it is a glass capillary ending 2 mm above the bottom and mounted in a glass joint, compare M L. Smith in G. Herdan, Small Particle Statistics, Elsevier Publ. Co., Amsterdam 1953, p. 471). The syphoning assembly also has a gas inlet. Pressurized nitrogen is admitted through this inlet to initiate the syphoning of the viscous fluid after exactly 7.5 minutes. The pressure must be adjusted such that the syphoning is completed within seven minutes. The liquid in the original bottle is then filled up again to 200 ml with butanolic Witcamide, a stopper is added, and the contents of the bottle are thoroughly mixed. The bottle is then rested for sedimentation at 37° C.

The above procedure is repeated after seven minutes with the syphoning started again at 7.5 minutes. If high purity in the separation is required, the sedimentation and syphoning after 7.5 minutes will have to be performed for a total of five times. A crude separation is obtained after two sedimentations. The final residue in the original bottle is then transferred back into the automatic Agate mortar, the ball of 70 mm diameter is added, and pulverization is continued for another 140 hours. The fractionation procedure is then repeated as described (above and also below; repetitions are done several times, until most of the original material is available in small particle size fractions).

The supernatants of the two (or five) sedimentations, which were syphoned off, are combined. The combined volume is reduced to 200 ml (for instance, by letting the suspension stand overnight and decanting the excess volume). The 200 ml new suspension are collected in another bottle of the type described above. A stopper is added and the liquid is thoroughly shaken. The bottle is then rested for sedimentation at 37° C.

After 14.5 minutes the stopper is carefully replaced by a syphoning assembly, as described above. Syphoning is initiated (with pressurized nitrogen) after exactly 15 minutes. The syphoning assembly is removed at the end and butanolic Witcamide is added up to the 200 ml mark. A stopper is added and the liquid is thoroughly shaken. The bottle is then rested for sedimentation at 37° C.

The above procedure is repeated after 14.5 minutes with the syphoning again started at exactly 15 minutes after mixing. If high purity separation is desired, sedimentation and syphoning after 15 minutes will have to be performed a total of five times. A crude separation is obtained after two sedimentations. The final residue in the bottle is transferred into a 5 ml graduated cylinder. By letting the cylinder stand and decanting off some supernatant, the suspension volume is reduced to 1 to 2 ml. Volume and weight of suspension are determined to allow the determination of the specific weight of the suspension. The actual yield may be determined from these numbers and from the known densities of the butanolic Witcamide and of the material fractionated. The viscosity of the medium is such that this size fraction has a particle radius of approximately 500 nm.

The supernatants of the two (or five) sedimentations, which were syphoned off, are combined. The combined volume is reduced to 200 ml (by letting the suspension stand overnight and decanting the excess volume). The 200 ml new suspension are collected in a new sedimentation bottle, as described before. A stopper is added, the liquid thoroughly shaken, and another sedimentation begun. This sedimentation is to last 30 minutes and is conducted as previously described. In this manner, many fractions are obtained. If the sedimentation time is increased by factor 2, the average radius of particles is decreased by 1.4142 factor. Pure n-butanol is used for fractions near 100 nm average radius with sedimentation times extending to 16 hours (over which time the bottle is kept in a box protected from thermal fluctuations).

Typical results from fractionations of the above kind follow. In the specific fractionation described, deriving from a fresh sample of material, these yields were obtained for the first two fractions: fraction between 7.5 and 15 minutes, 0.122 ml; fraction between 15 and 30 minutes, 0.0126 ml.

While in the foregoing I have disclosed embodiments of the invention in considerable detail for purposes of illustration, it will be understood by those skilled in the art that many of these details may be varied without departing from the spirit and scope of the invention.

I claim:

1. Magnetically-responsive discrete microparticles suitable for use in preparing selectively reversible suspensions thereof; each such microparticle having a core, a coating thereabout, and a diameter no greater than about one micron; said core being formed of a single particle of magnetically-responsive material having a Curie temperature within the range of about 5 to 65° C., a magnetic moment at saturation of at least 2.0 $\mu_B$ at 4.2° K, and a specific gravity above 3.0; said coating comprising a water-insoluble cross-linked polymeric material having reactive groups at the surface thereof.

2. The microparticles of claim 1 in which said magnetically-responsive material has a Curie temperature within the range of about 30 to 40° C.

3. The microparticles of claim 1 in which said coating has a thickness of at least 10% of the diameter of each of said microparticles.

4. The microparticles of claims 1 or 2 in which said magnetically-responsive core material is selected from the group consisting of ferrites, yttrium iron garnets, and alloys of $RMn_2X_2$ where R is a rare earth and X is germanium or silicon.

5. The microparticles of the alloy of claim 4 in which said rare earth is selected from the group consisting of lanthanum, praseodynium, and neodynium.

6. The microparticles of claim 1 in which said coating is a cross-linked acrylamide-based copolymer.

7. The microparticles of claim 1 in which said microparticles have an average size no greater than about 0.1 microns.

8. The microparticles of claim 1 in which the microparticles as coated have an average specific gravity greater than 3.0.

9. The microparticles of claim 1 in which the core of each microparticle has an average diameter of at least domain size.

10. A method for magnetically aggregating and thereafter suspending sub-micron-sized magnetizable particles, comprising the steps of forming each of said particles to have (a) a core of magnetically-responsive material with a Curie temperature within the range of about 5 to 65° C. and a saturation magnetic moment of at least 2.0 $\mu_B$ at 4.2° K and (b) a cross-linked polymeric coating about said core having reactive sites on the surface thereof; mixing said particles at a temperature not substantially below said Curie temperature with a first liquid medium containing a component capable of reacting with said coating; then exposing said particles to a magnetic field at a temperature not substantially exceeding said Curie temperature to cause magnetic aggregation of said particles; then separating the particles so aggregated magnetically from said first liquid medium, introducing said magnetically-aggregated particles into a second fluid medium, and subjecting the same to a temperature in excess of said Curie temperature in the absence of a magnetic field and with agitation to resuspend said particles in said second medium.

11. The method of claim 10 in which said step of exposing said particles to a magnetic field is undertaken at a temperature approximating said Curie temperature.

12. The method of claim 10 in which said step of exposing said particles to a magnetic field is undertaken at a temperature above said Curie temperature.

13. The method of claim 10 in which said magnetically-responsive material has a Curie temperature within the range of about 30 to 40° C.

14. A method of preparing a reversible suspension of coated magnetically-responsive microparticles, in which a magnetically-responsive core material is pulverized to produce core particles of a size substantially under 1.0 micron and said core particles are then each coated with a nonmagnetic polymeric material to form discrete coated magnetic microparticles having reactive groups at the surface thereof, wherein the improvement comprises forming said core particles of a magnetically-responsive material having a Curie temperature within the range of about 5 to 65° C., a magnetic moment at saturation of at least 2.0 $\mu_B$ at 4.2° K, and a specific gravity above 3.0; and carrying out said pulverizing and coating steps in a liquid medium at temperatures above the Curie temperature of said material.

15. The method of claim 14 in which there is an intervening step of fractionating said core particles immediately prior to said coating step, said fractionating step being carried out above said Curie temperature.

16. The method of claim 14 in which said magnetically-responsive material has a Curie temperature within the range of about 30° to 40° C.

17. The method of claim 15 in which said fractionating step is continued until the surface area of the largest core particles of a selected fraction is less than twice the surface area of the smallest particles of that fraction.

18. The method of claims 14, 15, or 16 in which there is a further step of fractionating said coated particles immediately following said coating step, said further step of fractionating said coated particles being carried out above said Curie temperature.

* * * * *